(12) United States Patent
Lai et al.

(10) Patent No.: US 6,852,331 B2
(45) Date of Patent: Feb. 8, 2005

(54) FABRICATION OF A CARTILAGE IMPLANT

(75) Inventors: Wen-Fu T. Lai, Taipei (TW); Ja-Reng Tang, Taipei (TW); Chien-Tsu Chen, Taipei (TW)

(73) Assignee: Taipei Biotechnology Ltd., Inc., Taipei (TW)

( * ) Notice: Subject to any disclaimer, the term of this patent is extended or adjusted under 35 U.S.C. 154(b) by 141 days.

(21) Appl. No.: 10/073,521

(22) Filed: Feb. 11, 2002

(65) Prior Publication Data

US 2003/0152556 A1 Aug. 14, 2003

(51) Int. Cl.$^7$ ............................ A61F 2/00; C12N 11/02; C12N 5/06; C12N 5/08
(52) U.S. Cl. ...................... 424/426; 424/93.7; 424/423; 435/177; 435/395
(58) Field of Search ................................ 435/177, 395; 424/423, 93.7, 426

(56) References Cited

U.S. PATENT DOCUMENTS

| | | | |
|---|---|---|---|
| 4,609,551 A | | 9/1986 | Caplan et al. ................. 424/95 |
| 4,642,120 A | | 2/1987 | Nevo et al. .................... 623/16 |
| 5,876,444 A | * | 3/1999 | Lai ............................. 424/423 |
| 6,530,956 B1 | * | 3/2003 | Mansmann .............. 623/18.11 |
| 6,623,963 B1 | * | 9/2003 | Muller et al. ................ 435/395 |

OTHER PUBLICATIONS

Folch, et al. *Stacks of Microfabricated Structures as Scaffolds for Cell Culture and Tissue Engineering.* Biomedical Microdevices 2(3):207–214 (2000).
Freed, et al. *Chondrogenesis in a Cell–Polymer–Bioreactor System.* Experimental Cell Research 240:58–65 (1998).
Freed, et al. *Joint resurfacing using allograft chondrocytes and synthetic biodegradable polymer scaffolds.* Journal of Biomedical Materials Research 28:891–899 (1994).
Gillogly, et al. *Treatment of Articular Cartilage Defects of the Knee With Autologous Chondrocyte Implantation.* JOSPT 28(4):241–251 (Oct. 1998).
Minas, et al. *Current Concepts in the Treatment of Articular Cartilage Defects.* Orthopedics 20(6):525–538 (Jun. 1997).
Peterson, et al. *Two– to 9–Year Outcome After Autologous Chondrocyte Transplantation of the Knee.* Clinical Orthopedics and Related Research 374:212–234 (2000).
Yasui, et al. *Primary Culture of Chondrocytes Embedded in Collagen Gels.* Expl. Cell Biol. 50:92–100 (1982).

* cited by examiner

Primary Examiner—David M. Naff
(74) Attorney, Agent, or Firm—Fish & Richardson P.C.

(57) ABSTRACT

A method of fabricating a cartilage implant including embedding and growing chondrocytes or mesenchymal stem cells in a three-dimensional substrate. The substrate contains randomly rewound α-helical monomers of type I collagen.

2 Claims, No Drawings

FABRICATION OF A CARTILAGE IMPLANT

BACKGROUND

Cartilage tissues have little self-repair capacity. Defects in cartilage tissues naturally heal to a limited degree with fibrocartilage, the biochemical, mechanical, and physiological properties of which are inferior to those of normal cartilage. Thus, damaged cartilage tissues are predisposed to degeneration.

Current therapies for cartilage regeneration include carbon plugs, periosteum, periochondrium, subchondral drilling, and autologous chondrocyte transplantation. However, most of them have failed to improve cartilage mechanics or physiology more than natural repair. The clinical need for improved treatment options has led to the development of cartilage implants fabricated in vitro from isolated chondrocytes or mesenchymal stem cells.

SUMMARY

The present invention relates to a cartilage implant.

In one aspect, this invention features a method of fabricating a cartilage implant by embedding chondrocytes or mesenchymal stem cells in a three-dimensional substrate. The substrate contains randomly rewound α-helical monomers of type I collagen, and optionally, can further contain randomly rewound α-helical monomers of type II collagen. The cell-substrate construct is placed in a culture medium. Mesenchymal stem cells can be induced to differentiate into chondrocytes by differentiation factors supplemented in the medium. As chondrocytes proliferate and differentiate in the substrate, they secret extracellular matrix proteins, e.g., proteoglycans and type II collagen, until a cartilage implant is produced.

The chondrocytes or mesenchymal stem cells, the type I collagen, and the type II collagen can be prepared from two or three different animal sources. For instance, chondrocytes isolated from humans can be used in combination with bovine type I collagen and type II collagen. The chrondrocytes or mesenchymal stem cells and the substrate can be placed in a rotating and oscillating vessel, which provides a permissive microenvironment for chondrogenesis, i.e., formation of cartilage.

Also within the scope of this invention is a cartilage implant fabricated according to the method described above. The cartilage implant contains chondrocytes embedded in a three-dimensional matrix, i.e., the extracellular component of the cartilage implant. The matrix differs from the substrate described above in composition. For example, it contains less amount of randomly rewound α-helical monomers of type I collagen due to degradation, and contains type II collagen synthesized by the embedded chondrocytes. The embedded chondrocytes include both those inside the matrix and those adhering to the surface of the matrix.

The present invention provides a method, which enables one to efficiently fabricate low-immunogenic cartilage implants. The details of some embodiments of the invention are set forth in the detailed description below. Other features, objects, and advantages of the invention will be apparent from the description, and from the claims.

DETAILED DESCRIPTION

The present invention features a method of fabricating a cartilage implant. Specifically, chondrocytes or mesenchymal stem cells are embedded in a three-dimensional substrate that contains randomly rewound α-helical monomers of type I collagen. Such a cell-collagen construct, when placed in a culture medium, grows to form a cartilage implant.

A substrate can contain either type I collagen alone, or both type I collagen and type II collagen. Type I collagen provides structural support in a cartilage implant of this invention. Type I collagen is the principle component of bone, skin, and tendon, and is the predominant type of collagen in a mature cicatrix, i.e., scar. It can be extracted and purified from tendon tissues (Lai, U.S. Pat. No. 5,876,444, 1999). Type II collagen is the major type of collagen in cartilage. Type II collagen helps to preserve the proliferation and differentiation abilities of chondrocytes or mesenchymal stem cells. It can be extracted and purified from cartilage tissues as described below.

In the method of this invention, the α-helical monomers of type I collagen and type II collagen are randomly rewound in the substrate. A cartilage implant produced from chondrocytes or mesenchymal stem cells embedded and grown in such a substrate shows unexpectedly low immunogenicity. Randomly rewound α-helical monomers of type I or type II collagen can be prepared as follows: (1) unwind the triple helices of type I or type II collagen by dissolving them in an acidic solution, and partially digesting them with a protease; and (2) allow the unwound α-helical monomers of type I or type II collagen to randomly rewind. See U.S. Pat. No. 5,876,444. When making a substrate containing both type I and type II collagen, the ratio of type II to type I collagen is, preferably, in the range of 1:1–1:2 (e.g., 1:1.2, 1:1.5, and 1:1.7) by weight. When unwound α-helical monomers of type I and type II collagen are mixed together, type I collagen monomers can wind with type II collagen monomers to form hybrid oligomers.

Chondrocytes and mesenchymal stem cells can be isolated from articular cartilage and bone marrow, respectively. Cells are cultivated to subconfluence, and then seeded in a substrate described above. The number of cells and the amount of substrate to be used can be determined empirically by a person skilled in the art, or by following the examples below. The cell-substrate construct thus obtained is placed in a culture medium and allowed to grow. When mesenchymal stem cells are used to fabricate a cartilage implant, the culture medium should include differentiation factors (e.g., IL-1 and dexamethasone) to induce the mesenchymal stem cells to differentiate into chondrocytes. One can grow the construct in a rotating and oscillating vessel. Unexpectedly, the construct grows much faster in a rotating and oscillating vessel than in a static flask. A cartilage implant forms in a few weeks. The cartilage implant can be stored at room temperature in a sealed, aseptic tissue culture media box for several days prior to being transported, molded, and implanted into a patient. When the cartilage implant is not used immediately after being transported to the patient site, it can be further stored in the above-described conditions for another few days.

The present invention also features a cartilage implant fabricated according to the method described above. Such an implant, when used to repair cartilage defects (e.g., in diarthrotic joints and the intervertebral disk), shows low-immunogenicity, even if the chondrocytes or mesenchymal stem cells, the type I collagen, and the type II collagen used to make the cartilage implant are prepared from different animal sources. For instance, chondrocytes isolated from rabbit articular cartilage can be mixed with type I collagen prepared from rat tails and type II collagen prepared from rabbit cartilage to produce a cartilage implant. Unexpectedly, such an implant can be used to repair cartilage defects in rabbit knee joints.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications recited herein are hereby incorporated by reference in their entirety.

Preparation of a Cartilage Implant (1) Type I Collagen Extraction and Purification Type I collagen was extracted and purified from tendons of New Zealand white rabbits or tendons of rat tails (Lai, U.S. Pat. No. 5,876,444, 1999). The tendons were dissected, sliced, and washed with several changes of cold distilled water to remove plasma proteins, and then extracted with 0.5 M NaCl in 50 mM Tris-HCl, pH 7.4 constantly stirred overnight at 4° C. The supernatant was decanted and the remainder was washed with several changes of cold distilled water to remove salts, and then incubated overnight at 4° C. in 0.5 M HOAc, pH 2.5 to obtain an aqueous extract. The extract was precipitated with a salt solution (0.9 M NaCl). The precipitate was centrifuged at 13,000 rpm for 30 min, and dissolved in 0.05 M HOAc to form a collagen-containing solution. Another salt solution (0.02 M $Na_2HPO_4$) was added twice to the collagen-containing solution over a 24 to 48 hr period for precipitation. The precipitate was centrifuged, and then dissolved in 50 mM HOAc to obtain another collagen-containing solution. The solution was dialyzed against 5 mM HOAc, and lyophilized.

(2) Type II Collagen Extraction and Purification

Type II collagen was prepared according to a modified Miller method (Methods Enzymol. 82:33–64). Rabbit cartilage was sliced and washed with 0.5 M NaCl and 20 mM EDTA in 0.05 M Tris buffer (pH 7.4). Glycoproteins were removed with 4M guanidine-HCl, and the extract was dissolved in 0.5 M acetic acid with 1 mg/ml pepsin. The collagen was precipitated by adding 0.9 M NaCl, washed with 70% alcohol several times to completely remove the acid and salt, and dissolved in 1 M NaCl and 0.05 M Tris buffer (pH 7.4). NaCl was added to 3.5 M for precipitation, and the supernatant was recovered. Type II collagen was then precipitated by adding NaCl to 4.5 M. The pellet was washed with 70% alcohol several times, and redissolved in 10 mM acetic acid to a final concentration of 2–4 mg/ml.

(3) Isolation and Cultivation of Chondrocytes

Chondrocytes were isolated from the articular cartilage of new borne New Zealand white rabbits (Lai, Doctoral Thesis of Medical Sciences, Faculty of Medicine, Harvard University, 1993). Tissue slices were incubated overnight in Hank's Balance Salt Solution (HBSS) containing 1 mg/ml hyaluronidase and 1 mg/ml collagenase. After centrifuging, the cell pellet was resuspended in DMEM with 10% FBS, 50 µg/ml gentamicin sulfate, 100 units/ml penicillin G sodium, 100 µg/ml streptomycin sulfate and 0.25 µg/ml fungizone. $5 \times 10^5$ cells were seeded per 10-cm petri dish, and were cultured in a 5% $CO_2$ incubator at 37° C. The medium was changed every 3–4 days, and the cells were grown until subconfluent.

(4) Preparation of Cartilage Implants

Both type I and type II collagen were sterilized with gamma radiation and dissolved in 5 mM HOAc, respectively. The collagen was partially digested with pepsin to remove the telopeptide. See, e.g., U.S. Pat. No. 5,876,444. The type I collagen-containing solution and the type II collagen-containing solution were gently mixed. Solutions were heated to 30–40° C. to facilitate mixing if necessary. The ratio of type II to type I collagen is 1:1–1:2 by weight.

1.0 ml of $(1-10) \times 10^6$ chondrocytes was mixed with another 1.0 ml solution containing 2–4 mg/ml type I and type II collagen. Chondrocytes were seeded in 24 rabbit substrates (i.e., substrates containing rabbit type I collagen and rabbit type II collagen) and 24 rat substrates (i.e., substrates containing rat type I collagen and rabbit type II collagen), respectively. The mixtures were placed in 6 or 24 well dishes until polymerized. The chondrocyte-collagen constructs were further incubated in DMEM containing specific nutrients including 10–20% fetal calf serum, HAM's F-12K, 0.3–0.5 mM proline, and 50–70 mg/L ascorbic acid; and drugs including 50 µg/ml gentamicin sulfate, 100 units/ml penicillin G sodium, 100 µg/ml streptomycin sulfate, and 0.25 µg/ml fungizone at 37° C. under 5% $CO_2$.

The chondrocyte-collagen constructs were first cultured in flasks for 3–5 days in a static manner. Half of them, i.e., 12 chondrocyte-rabbit substrate constructs and 12 chondrocyte-rat substrate constructs, were subsequently transferred into vessels gently rotated at 8–16 rpm with some degree of oscillation. The other half of the constructs remained in static flasks. The medium was changed every 2–4 days, and the chondrocyte-collagen constructs gradually became cartilage implants in two to four weeks.

Four chondrocyte-collagen constructs, i.e., a chondrocyte-rabbit substrate construct in a static flask, a chondrocyte-rat substrate construct in a static flask, a chondrocyte-rabbit substrate construct in a rotating and oscillating vessel, and a chondrocyte-rat substrate construct in a rotating and oscillating vessel, were removed in 1, 2, 3, and 4 weeks. The constructs were grossly examined and fixed in 10% formalin, embedded in paraffin and serially sectioned (Sacura Sledge microtome) at 5–10 microns. Tissue sections were stained with Hematoxylin/Eosin, and evaluated for chondrogenic differentiation.

(5) Immunohistochemistry

Tissue sections were incubated with a first antibody (anti-type II collagen and anti-chondroitin sulfate) or control blank serum. Type II collagen is the cartilage-specific component of the extracellular matrix. Chondroitin sulfate is the major composition of cartilage proteoglycan. The antigen-first antibody complexes were further incubated with a secondary antibody-horseradish peroxidase conjugate. Levels of type II collagen and chondroitin sulfate were determined by detecting the amount of the tertiary antigen-antibody complexes with 3,3' diaminobenzidine (DAB).

Histochemical results are summarized in Table 1 below.

TABLE 1

Chondrogenesis of chondrocyte-collagen constructs

| Container | Collagen substrate | Cultivation period | | | |
|---|---|---|---|---|---|
| | | 1 week | 2 weeks | 3 weeks | 4 weeks |
| Rotating and oscillating vessel | Rat substrate | Slight chondrogenesis | Hypertrophic chondrogenesis | Hypertrophic chondrogenesis | Hypertrophic chondrogenesis |

TABLE 1-continued

Chondrogenesis of chondrocyte-collagen constructs

| Container | Collagen substrate | Cultivation period | | | |
|---|---|---|---|---|---|
| | | 1 week | 2 weeks | 3 weeks | 4 weeks |
| Rotating and oscillating vessel | Rabbit substrate | No differentiation | Slight chondrogenesis | Hypertrophic chondrogenesis | Hypertrophic chondrogenesis |
| Static flask | Rat substrate | No differentiation | Slight chondrogenesis | Hypertrophic chondrogenesis | Hypertrophic chondrogenesis |
| Static flask | Rabbit substrate | No differentiation | No differentiation | No differentiation | Slight hypertrophic chondrogenesis |

Unexpectedly, chondrocyte-rat substrate constructs in rotating and oscillating vessels showed a slight chondrogenesis in one week, and hypertrophic chondrogenesis after 2 weeks. Chondrocyte-rabbit substrate constructs in rotating and oscillating vessels and chondrocyte-rat substrate constructs in static flasks both started slight chondrogenesis in 2 weeks, and showed hypertrophic chondrogenesis after 3 weeks. Chondrocyte-rabbit substrate constructs in static flasks did not show chondrogenesis until after 3 weeks; however, slight hypertrophic chondrogenesis was noted by the fourth week.

Generally, more lacunae formation surrounding chondrocytes was found in constructs grown in rotating and oscillating vessels than those in static flasks. Most chondrocyte-collagen constructs in all groups showed a cartilage-like appearance in 4 weeks. Immunohistochemical evaluation showed that type II collagen and chondroitin sulfate were present in all hypertrophic chondrocyte-collagen constructs.

Cartilage Repair (1) Cartilage Defect and Implantation

Thirty-six male New Zealand white rabbits were used in this experiment. Each rabbit weighed around 2.5 kg, and the average age was 4-month old. The rabbits were anesthetized by intramuscular injection of a mixture of Ketamine (100 mg/ml, 0.65 ml/kg body weight) and Xylazine (20 mg/ml, 0.30 ml/kg body weight). The skin around one knee was shaved anteriorly and washed with iodine. A parapatellar medial method was used to approach the knee joint. The patella was dislocated, and a 4 mm circular full-thickness defect in the articular cartilage was generated with a 4 mm drill. A hole was introduced in the medial femoral condyle. The cone-shaped defect was made 4 mm deep and extending into the cancellous bone in the bone marrow cavity. To avoid confounder effect, half of the rabbits had a defect made in the right knee joint, and the other half in the left knee joint.

The defect was repaired with a cartilage implant described above. Twelve rabbits were treated with chondrocyte-rabbit matrix implants (CRBTCM). Another 12 rabbits were treated with chondrocyte-rat matrix implants (CRTTCM). The remaining 12 rabbits, as a surgery control group, were not treated with implants. The knee joint without a surgery was used as an intact knee joint control.

Cartilage repair was examined 1, 2, or 3 months after the surgery. Three rabbits in each group were sacrificed each time. The knee joints were end bloc removed and examined microscopically. The distal part of the femur was fixed with formalin, decalcified, and sectioned sagittally, perpendicular to the defect. These sections were obtained from the center of the defect. The specimens were stained with Hematoxylin/Eosin and examined microscopically.

(2) Microscopic Examination

Normal articular cartilage appears semi-transparently white with yellowish cast, covering the articulating end of the femoral condyle. The surgical defects without implantation appeared concave, and were filled with white shining tissues at 4 weeks. The margin of the defect was well defined. At 12 weeks, the surface of the defect became irregularly shaped with fibrosis.

Unexpectedly, no signs of osteoarthritis, such as osteophytes, cartilage erosion, or synovial proliferation, were observed in the operated knees of both CRBTCM and CRTTCM groups. The defects were filled with white opaque tissues 4 weeks after surgery. After 12 weeks, both groups showed cartilage-like tissues covering the surgical sites. The reparative tissues appeared semi-transparent and the margins were integrated with adjacent healthy tissues.

(3) Histology

The surgery control group: Mild degeneration, fibrillation and fragmentation of cartilage were found in the wound and adjacent areas after one month. The defect was repaired by fibroblast combined with sparse chondroblast ingrowth. After two months, moderate to severe cartilage degeneration, fibrillation and fragmentation of cartilage were noted in the wound and adjacent areas. The defect was repaired by fibrosis and partial chondroblast ingrowth. The subchondral bone of the defect was denuded and covered by fibrous tissues after three months.

The CRBTCM and CRTTCM groups: Unexpectedly, after one month, the defect was predominantly filled with chondroblasts. The cellular morphology of chondrocytes varied from round to polygonal-like. The chndroblasts penetrated into the subchondral layer. Mild inflammation was noted at the bottom of the implantation site in both groups.

After two months, more fibrocartilage was noted compared to that of the one-month group. Also, more fibrocartilage was found in the CRTTCM group than in the CRBTCM group. In addition, moderate inflammation was found at the implantation site in the CRTTCM group, whereas only mild inflammation was found at the implantation site in the CRBTCM group.

After three months, the defects were repaired by resembled fibrous cartilage in both CRTTCM and CRBTCM groups. The cartilage implant was thinner than the surrounding adjacent normal cartilage. At the edge of the defect, the cartilage implant integrated with the adjacent healthy tissues. No inflammatory response was found in either group.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method of fabricating a cartilage implant comprising:
    embedding chondrocytes or mesenchymal stem cells in a three-dimensional substrate, the substrate containing randomly rewound α-helical monomers from partially digested type I collagen; and
    growing the chondrocytes or mesenchymal stem cells in the substrate, thereby producing a cartilage implant;
    wherein, during the growing step, the chrondrocytes or mesenchymal stem cells and the substrate are placed in a rotating and oscillating vessels.

2. A method of fabricating a cartilage implant comprising:
    embedding chondrocytes or mesenchymal stem cells in a three-dimensional substrate, the substrate containing randomly rewound α-helical monomers from partially digested type I collagen; and
    growing the chondrocytes or mesenchymal stem cells in the substrate, thereby producing a cartilage implant;
    wherein the substrate further contains randomly rewound α-helical monomers from partially digested type II collagen, and during the growing step, the chrondrocytes or mesenchymal stem cells and the substrate are placed in a rotating and oscillating vessel.

* * * * *